US009744235B2

(12) United States Patent
Po

(10) Patent No.: US 9,744,235 B2
(45) Date of Patent: Aug. 29, 2017

(54) TREATMENT OF CARDIOVASCULAR DISORDERS WITH TARGETED NANOPARTICLES

(71) Applicant: The Board of Regents of the University of Oklahoma, Norman, OK (US)

(72) Inventor: Sunny Po, Edmond, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 14/104,422

(22) Filed: Dec. 12, 2013

(65) Prior Publication Data

US 2014/0100411 A1 Apr. 10, 2014

Related U.S. Application Data

(63) Continuation-in-part of application No. 12/907,806, filed on Oct. 19, 2010, now Pat. No. 8,740,872.

(60) Provisional application No. 61/836,392, filed on Jun. 18, 2013.

(51) Int. Cl.
| | | |
|---|---|---|
| *A61M 31/00* | (2006.01) | |
| *A61K 41/00* | (2006.01) | |
| *A61N 2/00* | (2006.01) | |
| *A61K 47/48* | (2006.01) | |
| *A61K 9/00* | (2006.01) | |
| *A61K 9/50* | (2006.01) | |
| *A61K 9/51* | (2006.01) | |
| *A61K 33/06* | (2006.01) | |
| *B82Y 5/00* | (2011.01) | |

(52) U.S. Cl.
CPC ............ *A61K 41/00* (2013.01); *A61K 9/0009* (2013.01); *A61K 9/0019* (2013.01); *A61K 9/5094* (2013.01); *A61K 9/5115* (2013.01); *A61K 33/06* (2013.01); *A61K 47/48769* (2013.01); *A61N 2/002* (2013.01); *B82Y 5/00* (2013.01)

(58) Field of Classification Search
CPC .. A61K 9/0009; A61K 9/0019; A61K 9/5094; A61K 9/5115; A61K 33/06
USPC ...................................................... 604/507
See application file for complete search history.

(56) References Cited

U.S. PATENT DOCUMENTS

| | | | |
|---|---|---|---|
| 5,427,767 A | 6/1995 | Kresse et al. | |
| 5,705,195 A | 1/1998 | Volkonsky et al. | |
| 6,048,515 A | 4/2000 | Kresse et al. | |
| 6,200,547 B1 | 3/2001 | Volkonsky et al. | |
| 6,514,481 B1 | 2/2003 | Prasad et al. | |
| 6,743,779 B1 | 6/2004 | Unger et al. | |
| 6,977,080 B1 | 12/2005 | Donovan | |
| 7,485,624 B2 | 2/2009 | Donovan | |
| 7,709,440 B2 | 5/2010 | Shaari | |
| 7,723,311 B2 | 5/2010 | Seeney et al. | |
| 7,731,977 B2 | 6/2010 | Ackerman | |
| 2005/0175703 A1 | 8/2005 | Hunter et al. | |
| 2006/0002852 A1 | 1/2006 | Saltzman et al. | |
| 2006/0025713 A1 | 2/2006 | Rosengart et al. | |
| 2006/0057211 A1 | 3/2006 | Chorny et al. | |
| 2006/0228421 A1 | 10/2006 | Seeney et al. | |
| 2007/0196281 A1 | 8/2007 | Jin et al. | |
| 2008/0241262 A1 | 10/2008 | Lee et al. | |
| 2009/0082611 A1* | 3/2009 | Levy et al. ............... 600/9 |
| 2009/0216320 A1 | 8/2009 | Levy et al. | |
| 2009/0226521 A1 | 9/2009 | Smyth et al. | |
| 2009/0287036 A1 | 11/2009 | Shapiro et al. | |
| 2010/0036480 A1 | 2/2010 | Viller et al. | |
| 2010/0079142 A1 | 4/2010 | Fontius | |
| 2010/0204674 A1 | 8/2010 | Forbes et al. | |

OTHER PUBLICATIONS

Weissleder et al., "Superparamagnetic Iron Oxide: Pharmacokinetics and Toxicity." *AJR* 152:167-173, (1989).
Forbes et al., "An Approach to Targeted Drug Delivery Based on uniform Magnetic Fields." IEE Transactions on Magnetics, vol. 39, No. 5, Sep. 2003.
Douziech-Eyrolles et al., "Nanovectors for anticancer agents based on superparamagnetic iron oxide nanaparticles." International Journal of Nanomedicine: 2 (4), pp. 541-550, (2007).
Hou et al., "Ganglionated Plexi Modulate Extrinsic Cardiac Autonomic Nerve Input." Journal of the American College of Cardiology by the American College of Cardiology Foundation, Elsevier Inc., vol. 50, No. 1, (2007).
Forbes et al., "Validation of High Gradient Magnetic Field Based Drug Delivery to Magnetizable Implants Under Flow." IEEE Transactions on Biomedical Engineering, vol. 55, No. 2, Feb. 2008.
Avilés et al., "Isolated swine heart ventricle perfusion model for implant assisted-magnetic drug targeting." International Journal of Pharmaceutics 361, pp. 202-208, Elsevier B.V., (2008).
Basak et al., "Transport characteristics of nanoparticle-based ferrofluids in a gel model of the brain." International Journal of Nanomedicine, Dover Medical Press Ltd., vol. 4, pp. 9-26, (2009).
Polyak et al., "Magnetic targeting for site-specific drug delivery: applications and clinical potential." Informa Healthcare, London, vol. 6, pp. 53-70, Issued Jan. 2009.
Kumar et al., "Multifunctional magnetic nanoparticles for targeted delivery." Nanomedicine: NBM, vol. 6, pp. 64-69, doi:10.1016/j, (2010).
Hoare et al., "A Magnetically Triggered Composite Membrane for On-Demand Drug Delivery." American Chemical Society, Nano Letters, vol. 9, No. 10, pp. 3651-3657, (2009).

(Continued)

*Primary Examiner* — Edelmira Bosques
(74) *Attorney, Agent, or Firm* — Dunlap Codding, P.C.

(57) ABSTRACT

Methods for treating various cardiovascular disorders include targeted delivery of calcium ions for permanently impairing a portion of the autonomic nervous system (ANS). Targeted delivery may be via magnetically-targetable nanoparticles.

13 Claims, No Drawings

(56) References Cited

OTHER PUBLICATIONS

Chorny et al., "Targeting stents with local delivery of paclitaxel-loaded magnetic nanoparticles using uniform fields." PNAS, vol. 107, No. 18, pp. 8346-8351, May 2010.
Yu et al., "Autonomic Denervation Using Magnetic Nanoparticles." Heart Rhythm Society, Heart Rhythm Journal, vol. 7, Issue 5S, P01-13, May 2010.
Petros et al., "Strategies in the design of nanoparticles for therapeutic applications." Macmillan Publishers Limited, Nature Reviews, Drug Discovery, vol. 9, pp. 615-627, Aug. 2010.

\* cited by examiner

TREATMENT OF CARDIOVASCULAR DISORDERS WITH TARGETED NANOPARTICLES

CROSS-REFERENCE TO RELATED APPLICATIONS/INCORPORATION BY REFERENCE STATEMENT

The present application claims benefit under 35 U.S.C. §119(e) of U.S. Provisional Application Ser. No. 61/836,392, filed Jun. 18, 2013. The present application is also a continuation-in-part of U.S. Ser. No. 12/907,806, filed Oct. 19, 2010. The entire contents of each of the above-referenced patents and patent applications are hereby expressly incorporated herein by reference.

BACKGROUND

Many cardiovascular diseases are caused by the hyperactivity of the ANS, including such disorders as cardiac arrhythmias including (but not limited to) atrial and ventricular fibrillation and tachycardia, vasovagal syncope, inappropriate sinus tachycardia and hypertension. Atrial fibrillation (AF) is the most common cardiac arrhythmia requiring treatment and frequently progresses from paroxysmal AF to permanent AF. AF accounts for nearly 20% of the strokes in the U.S. AF inflicted approximately 2.3 million Americans in 2004 and costs the health care system nearly $12 billion a year to treat AF and AF-related strokes. By the year 2050, the number of AF patients is projected to increase to 16 million as the population ages. Nearly half of AF patients are refractory (i.e., do not respond) to antiarrhythmic drugs and require non-pharmacologic treatment, i.e., surgical or catheter ablation. Clinical trials aimed at a pharmacological treatment of AF resulted in a 50% success rate after one year follow-up. The other 50% have been shown to have drug and cardioversion resistance. These patients are now treated with costly and time consuming catheter-based application of radiofrequency (RF) energy within the heart to isolate the focal firing sites in the pulmonary vein (PV) myocardial sleeves from the rest of the atria.

Currently, there is only one RF ablation catheter approved by the FDA for atrial ablation procedures. Off-label use of all other catheter and surgical ablation devices had raised significant regulatory concerns and litigations. Standard catheter or surgical ablation procedures produce lesion sets to isolate the pulmonary vein (PV)-atrial junction, containing the presumed triggers and/or substrate for AF. However, in a single procedure, PV antrum isolation only leads to less than 50% success at 5 years for the earliest stage of AF (paroxysmal AF) and approximately 30% for more persistent forms of AF. This approach, widely practiced worldwide, has many drawbacks including a relatively low success rate (~70%) and various complications, including PV stenosis, cardiac tamponade, esophageal injury and minor or major strokes. Despite all the advances in ablation technologies in the past 8 years, success of AF ablation has not improved. The unsatisfactory efficacy of AF ablation is mainly due to insufficient understanding of the electrophysiological mechanism(s) underlying the initiation of AF and its progression into more persistent forms of AF. A mechanistically-based therapy is still lacking.

Prior studies of AF initiation in patients and animals indicate that (unbalanced) activation of both sympathetic and parasympathetic nervous systems often precede AF onset. Mammalian hearts are dually innervated by the extrinsic and intrinsic cardiac autonomic nervous system (CANS). It is known that the intrinsic CANS is a neural network composed of many ganglionated plexi and interconnecting nerves and/or neurons. In this neural network, bilateral autonomic inputs come together at many "integration centers" before giving rise to final common pathways that control cardiac rhythm and force of contraction. These intrinsic integration centers are located in epicardial ganglionated plexi (GP) or ligament of Marshall which are overlain by epicardial fat pads. In mammalian hearts, the ligament of Marshall and four major atrial GP (anterior right GP, ARGP; inferior right GP, IRGP; superior left GP, SLGP; and inferior left GP, ILGP) are located adjacent to the junction of the atrium and four pulmonary veins. Stellate ganglia, the gateway of sympathetic innervation to the heart, are located just above the apex of the lung. In previous studies, the inventors have shown that electrical stimulation or injection of acetylcholine into the GP near the PV-atrial junction can initiate sustained AF arising from the PV-atrial junction. Ablation of the four major atrial GP and ligament of Marshall markedly suppressed the inducibility and maintenance of AF in multiple animal models, including the rapid atrial pacing model. Notably, the lesion sets of a standard RF ablation (PV antrum isolation) involve ablation of two or three of the four major atrial GP, the ligament of Marshall, and numerous autonomic nerves, indicating that autonomic denervation is a major contributor to the antiarrhythmic effects of AF ablation. Importantly, ablations involving only the major atrial GP, without PV antrum isolation, yielded similar results to the standard PV antrum isolation but produced significantly less collateral damage to the atrial myocardium and possibly less consequent iatrogenic left atrial flutter. While re-innervation may occur 3-6 months after RF catheter ablation procedures, the clinical benefits of GP ablation lasted 16-18 months, suggesting that permanent injury to the autonomic neurons in intrinsic CANS may underlie the therapeutic effects of ablation because unlike nerves, neurons seldom regenerate.

Targeted drug delivery is an increasingly used nanomedicine technology in which delivery of therapeutics to target tissues may increase drug efficacy, eliminate side effects, and reduce costs. Polymeric nanoparticles whose diameters can range from 10-300 nanometers can be formulated as nanocomposites with encapsulated drugs for burst and controlled release. Superparamagnetic nanoparticles, approved in the early 1990s for clinical magnetic resonance imaging enhancement, can be encapsulated in polymers, silicon, or carbohydrates and pulled into tissues to produce more precise lesion sets, thereby reducing non-specific damages.

Standard RF ablation requires the creation of two circumferential lesions to isolate the antrum of all the PVs. Currently, atrial ablation strategies focus on isolating and/or destroying atrial tissue that presumably is responsible for AF, although the long-term consequences of extensive damage to the atrial myocardium, neural elements, and atrial contractility are yet to be discovered.

Multiple basic science studies have demonstrated a significant impact on AF after the major left atrial GPs were ablated. Using a rapid atrial pacing model, Lu et al. (Cardiovas. Res., 84:245-52 (2009)) showed that shortening of the effective refractory period (ERP) and an increase of ERP dispersion, as well as increased AF inducibility caused by rapid atrial pacing for 3 hours, were all reversed by ablation of the 4 major atrial GP and the ligament of Marshall (LOM). In animals receiving GP ablation first, rapid atrial pacing for 6 hours failed to change the ERP, ERP dispersion, and AF inducibility. Other animal studies also demonstrated that after ablation of the GP and LOM, AF became more difficult to initiate and sustain. AF often terminated after GP ablation. The inventors proposed that autonomic denervation may serve as a therapeutic modality to prevent paroxysmal AF to progress to more persistent forms of AF. Moreover, GP ablation may also convert AF from the focal form of AF to the macro-reentrant form of AF, which is more responsive to antiarrhythmic drugs.

Several clinical studies have indicated the benefits of autonomic denervation by targeting the major atrial GPs identified by high frequency stimulation. When GP ablation was combined with PV isolation, the success rate is significantly better than PV isolation alone. A series of recent manuscripts by Pokushalov et al. (*Heart Rhythm*, 6:1257-64 (2009); *Asian Cardiovasc Thorac Ann*, 16:194-201 (2008); and *Europace*, 12:342-346 (2010)) also reported similar success rates in AF ablation targeting only the major atrial GPs in comparison to the standard PV isolation approach.

As noted, clinical studies demonstrated that GP ablation as an adjunct therapy to PV isolation improved the outcome of AF ablation, whereas GP ablation alone produced a success rate similar to the standard PV isolation. This denervation-only ablation strategy has the advantage of producing more focused lesion sets and potentially carrying a smaller risk of producing iatrogenic macro-reentrant left atrial tachycardia.

A method of direct (targeted) treatment of specific portions of the ANS for the inhibition of various disorders, such as cardiovascular disorders involving the ANS, particularly for permanent inhibition of those portions of the ANS, would be highly desirable.

DETAILED DESCRIPTION

Before explaining at least one embodiment of the presently described inventive concept(s) in detail by way of exemplary drawings, description, experimentation, results, and/or laboratory procedures, it is to be understood that the inventive concept(s) is not limited in application to the details of construction and the arrangement of the methods, processes, compositions, and components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting except where indicated as such.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized herein are those well known and commonly used in the art. The nomenclatures utilized herein are those well known and commonly used in the art.

All patents, published patent applications, and non-patent publications mentioned in the specification are indicative of the level of skill of those skilled in the art to which the presently disclosed and claimed inventive concept(s) pertain. All patents, published patent applications, and non-patent publications referenced in any portion of this application are herein expressly incorporated by reference in their entirety to the same extent as if each individual patent or publication was specifically and individually indicated to be incorporated by reference. In particular, as noted above, U.S. Ser. No. 12/907,806 filed on Oct. 19, 2010, is explicitly incorporated by reference herein in its entirety.

All of the devices, apparatus, compositions, and/or methods disclosed herein can be made and executed without undue experimentation in light of the present disclosure. While the compositions and methods of this disclosure have been described in terms of particular embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the inventive concept(s) as disclosed herein.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The term "about" is used to indicate that a value includes the inherent variation of error for the device, composition, or the method being employed to determine the value and/or the variation that exists among study items. As used herein, the term "substantially" means that the subsequently described event or circumstance completely occurs or that the subsequently described event or circumstance occurs to a great extent or degree. For example, the term "substantially" means that the subsequently described event or circumstance occurs, in certain embodiments, at least 90% of the time, or at least 95% of the time, or at least 98% of the time.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, BBC, AAABCCCC, CBBAAA, CABABB, and so forth. The skilled artisan will understand that typically there is no limit on the number of items or terms in any combination, unless otherwise apparent from the context.

Where used herein the term "subject" refers to animals having an ANS, particularly mammals, and more particularly to humans, primates, apes, monkeys, dogs, cats, horses, lab animals including, mice, rats, guinea pigs, and rabbits, livestock animals including cows, sheep, and goats, and zoo animals.

While the presently disclosed and claimed inventive concept(s) will now be described in connection with particular examples and embodiments so that aspects thereof may be more fully understood and appreciated, it is not intended to limit the presently disclosed and claimed inventive concept(s) to these particular examples and embodiments. On the contrary, it is intended to cover all alternatives, modifications and equivalents as may be included within the scope of the presently disclosed and claimed inventive concept(s) as described herein. Thus, the following description serves to illustrate the practice of this presently disclosed and claimed inventive concept(s), it being understood that the particular examples and embodiments shown and discussed are by way of example and for purposes of illustrative discussion of the presently disclosed and claimed inventive concept(s) only and are presented in the cause of providing what is believed to be useful and readily understood description of formulation procedures and methods of treatment as well as of the principles and conceptual aspects of the presently disclosed and claimed inventive concept(s).

The presently disclosed and claimed inventive concept(s) relates to targeted therapeutic delivery systems and methods to treat cardiovascular disorders, and in particular, use of targeted nanoparticles to denervate specific portions of the autonomic nervous system (ANS) for treating cardiovascular disorders involving the autonomic nervous system.

Targeted drug delivery is an emerging technology in which therapeutic delivery to tissues can increase drug efficacy, alleviate side effects, and reduce costs. Polymeric nanoparticles can be formulated with absorbed, adsorbed, attached, embedded, or encapsulated drugs for burst and controlled release. In the presently disclosed and claimed inventive concept(s), targeted (such as magnetically-targeted) delivery of calcium (particularly $Ca^{2+}$ ions) is used to treat various cardiovascular disorders, such as but not limited to, arrhythmias.

Thus, at least one embodiment of the present disclosure includes a method for targeted delivery of a permanently-acting neurotoxic agent (in high extracellular and intracellular concentrations) to specific areas of the ANS including, but not limited to, portions of the intrinsic cardiac autonomic nervous system such as the atrial ganglionated plexi (GP), ligament of Marshall, or the left and right stellate ganglia. The permanently-acting neurotoxic agent comprises releasable calcium $Ca^{2+}$ ions; non-limiting examples of permanently-acting neurotoxic agents that may be utilized in accordance with the presently disclosed and claimed inventive concept(s) include calcium compounds, such as but not limited to, calcium chloride ($CaCl_2$), calcium carbonate ($CaCO_3$), calcium citrate, calcium gluconate, calcium formate, calcium citrate malate, calcium bis-glycinate, calcium lactate, calcium orotate, calcium fumarate, calcium fluoride, calcium ascorbate, calcium succinate, and calcium aspartate, as well as any combination thereof. Calcium-induced apoptosis of the atrial GP (such as, but not limited to, via magnetically-targeted, magnetically-susceptible nanoparticles delivering calcium ions) can effectively inhibit or stop the activity of GP, ligament of Marshall, or the left and right stellate ganglia and the related cardiovascular diseases thereto without permanent damage to other portions of the intrinsic CANS or to myocardium.

More particularly, the presently disclosed and claimed inventive concept(s) includes methods which use a calcium compound as the payload of nanoparticles (which in one embodiment are magnetic) or other targeted drug delivery systems to injure neural tissues in order to treat cardiovascular diseases that are caused by hyperactivity of the autonomic nervous system. It is known that increased intracellular calcium is toxic to cells, and in particular, neurons. Higher than normal calcium ion concentrations have been viewed as a "toxin" to neural tissues. The presently disclosed and claimed inventive concept(s) utilizes the property of calcium-mediated neurotoxicity to mitigate and/or eliminate the abnormally high neural activity that leads to cardiovascular diseases such as, but not limited to, hypertension, vasovagal syncope, and cardiac arrhythmias. The nanoparticles described or enabled herein may be administered to the subject in the form of compositions in which the nanoparticles are disposed in a pharmaceutically-acceptable carrier or vehicle. Non-limiting examples of pharmaceutically-acceptable carriers or vehicles that may be use in accordance with the presently disclosed and claimed inventive concept(s) include, but are not limited to, saline, phosphate-buffered saline, or any other such carrier or vehicle known in the art for such purposes. In one embodiment, the magnetic nanoparticles (MNPs), comprised of polymer encapsulant, iron-containing smaller core nanoparticles and therapeutic payload (i.e., the calcium compound) are administered in dosages in a range of from about 0.01 mg to about 10 mg, in a range of from about 0.1 mg to about 5 mg, or in a range of from about 0.5 mg to about 2.5 mg.

The methods described herein have wide commercial applications since calcium is cationic, regulated, and naturally present in humans. The amount of calcium needed to injure a discrete area of neural tissue may be only a few milligrams in order to reach a local concentration of 5 mM, far below the amount of daily calcium intake (>500 mg) recommended to prevent osteoporosis. In certain embodiments, the amount of calcium needed to injure a discrete area of neural tissue (e.g., 0.1 to 4 $cm^2$) may be only a few milligrams.

In the presently disclosed and claimed inventive concept(s), a calcium compound which releases $Ca^{2+}$ ions is used as the payload in a targeted drug-delivery system, such as but not limited to, nanoparticles (magnetic or non-magnetic), liposomes, dendrimers, or any other type of drug-delivery system capable of functioning as described herein. After the vehicles of delivery are navigated to the targets (e.g., via cannulation, catheterization, or magnetism), the payload (i.e., a calcium compound) will be released and incorporated by the targeted cells, and the intracellular calcium concentration in the targeted cell will increase substantially. Elevated intracellular calcium subsequently activates a series of enzymes and eventually causes cellular injury and death of the cell by apoptosis.

Atrial fibrillation, one example of a cardiovascular disorder, is the most commonly encountered cardiac arrhythmia and affects 2.5 million people in the United States alone. As the population ages, the incidence is projected to increase to 16 million in year 2050, a significant portion of whom will have drug-refractory AF and require ablation. Catheter or surgical ablation carries significant risks of serious complications and is very costly. Targeted drug delivery as described in the present disclosure provides a less invasive and less expensive therapeutic modality. With the advances in stereotactic localization by an externally applied magnetic field, it is possible to target (deliver selectively) the MNPs to one or more GPs, ligament of Marshall, or stellate ganglia to achieve autonomic denervation and treat AF without the risks of serious complications associated with catheter or surgical ablation or the side effects associated with long-term anti-arrhythmic therapy.

Embodiments of the methods of the presently disclosed and claimed inventive concept(s) include but are not limited to:

(1) Treatment of atrial fibrillation and syncope: The targets are the plurality of clusters of cardiac autonomic neurons, including interneurons and neurons in the GP that provide the neural control of cardiac electrophysiology, vascular tone, and contractility. Hyperactivity of these ganglionated plexi leads to hyperactivity of much of the cardiac autonomic nervous system and can cause atrial fibrillation and syncope. A standard coronary angiogram catheter is cannulated into the coronary artery supplying the plurality of ganglionated plexi. In the presence of focused electromagnetic force, magnetic nanoparticles are slowly infused into the coronary artery. Magnetic nanoparticles carrying the calcium payload are conveyed by the microcirculation to the targeted ganglionated plexi and release the calcium payload to cause neurotoxicity.

(2) Treatment of hypertension: The targets are the sympathetic nerves and neurons that control blood pressure, particularly the ones surrounding the renal arteries. An angiogram catheter suitable for size of the targeted artery is selectively engaged into the artery supplying the sympathetic neurons or nerves. The electromagnetic force focuses on the targeted sympathetic nerves or neurons, and magnetic nanoparticles carrying the calcium payload are slowly infused into the artery and navigate to the targeted neural tissues to release the calcium to cause neurotoxicity. In the case of renal sympathetic denervation, the renal artery is cannulated to allow the calcium payload to denervate the renal sympathetic nerves and neurons.

(3) Treatment of ventricular tachycardia/fibrillation: Ventricular tachycardia/fibrillation, the leading cause of sudden death, is often triggered by high sympathetic activity. The ventricles receive sympathetic innervation from the left and right stellate ganglia as well as their major branches, the ventromedial cardiac nerve and the ventrolateral cardiac nerve, all of which can be selectively injured by the presently described target drug deliver therapy. One of the most suitable targets for sympathetic denervation by targeted drug therapy is to denervate the ventrolateral cardiac nerve (VLCN). This nerve (VLCN) travels within the vein of Marshall, which can be selectively cannulated through the right atrium and coronary sinus. When the magnetic nanoparticles are slowly infused into the vein of Marshall, the electromagnet can sequentially focus on different segments of the vein of Marshall to denervate the entire vein of Marshall and the VLCN within it. Denervation of the VLCN leads to long-term suppression of catecholamine release at the left ventricular, thereby eliminating the triggers for ventricular tachycardia/fibrillation.

(4) Treatment of inappropriate sinus tachycardia: Inappropriate sinus tachycardia (IST) is a very vexing disease resulting from hyperactivity of the sympathetic tone. In the resting state, the sinus rate is often faster than 100 beats per minutes. With minimal exertion, the sinus rate quickly increases to 130-150 beats per minutes. This disease is often refractory to pharmacological therapy. The result of catheter ablation was so poor that it is rarely performed today. The right stellate ganglion and ARGP as well as the interganglionic nerve between the two ganglia have been shown to underlie the sinus tachycardia. In the presence of focused electromagnetic force, magnetic nanoparticles presently described are slowly infused into the arteries supplying the right stellate ganglion or ARGP. Magnetic nanoparticles of the present disclosure carrying the calcium payload navigate to the targeted ganglionated plexi and release the calcium payload to cause neurotoxicity.

In one embodiment, the presently disclosed and claimed inventive concept(s) is for the purpose of preventing or reducing atrial arrhythmias in patients, especially atrial fibrillation. The presently disclosed and claimed inventive concept(s) includes methods for applying MNPs, via the vascular system, and targeting them to one or more of the four ganglionated plexi and/or the ligament of Marshall on the epicardial surface of the heart, thus allowing release of the calcium agent for causing permanent neuropathy (injury) to the site of action. Additionally, the embolization of the microcirculation by the MNPs may also cause ischemia and subsequent selective temporary or permanent neuropathy of autonomic neurons in the GP. Additionally, the alternating electromagnetic oscillation of the MNPs optionally will allow for controlled warming and thus controlled release of the bioactive agent by elevating the temperature of the MNPs, thereby causing swelling or contraction of a matrix component of the MNPs.

Millions of patients who have atrial arrhythmias have few or no alternatives to cure the atrial fibrillation. The methods of the presently disclosed and claimed inventive concept(s) employ, to various degrees, nanotechnology, magnetic targeting, catheterization, cannulation, a nanocomposite calcium compound delivery system, temperature-controlled release of calcium ions from the calcium compound, and microvascular embolization, all for the purpose of selectively reducing the (autonomic) activity emanating from (intrinsic autonomic) GP, which in combination with the extrinsic autonomic innervation of the heart is responsible for cardiac arrhythmias, especially those of the atria.

As described elsewhere herein, MNPs used in the presently disclosed and claimed inventive concept(s) generally comprise a biocompatible polymeric matrix component which contains one or more magnetically-susceptible core particles (e.g., iron oxides). The MNPs also contain and transport the calcium compound. The biocompatible polymeric matrix component may be biodegradable. In non-limiting embodiments, the nanoparticles formed by the matrix component, magnetically-susceptible core particles, and calcium compound typically have diameters in a range of from about 100 to about 500 nm.

For example, MNPs of the presently disclosed and claimed inventive concept(s) in various embodiments may have major diameters in the range of about 100 nm to about 110 nm, about 110 nm to about 120 nm, about 120 nm to about 130 nm, about 130 nm to about 140 nm, about 140 nm to about 150 nm, about 150 nm to about 160 nm, about 160 nm to about 170 nm, about 170 nm to about 180 nm, about 180 nm to about 190 nm, about 190 nm to about 200 nm, about 200 nm to about 210 nm, about 210 nm to about 220 nm, about 220 nm to about 230 nm, about 230 nm to about 240 nm, about 240 nm to about 250 nm, about 250 nm to about 260 nm, about 260 nm to about 270 nm, about 270 nm to about 280 nm, about 280 nm to about 290 nm, about 290 nm to about 300 nm, about 300 nm to about 310 nm, about 310 nm to about 320 nm, about 320 nm to about 330 nm, about 330 nm to about 340 nm, about 340 nm to about 350 nm, about 350 nm to about 360 nm, about 360 nm to about 370 nm, about 370 nm to about 380 nm, about 380 nm to about 390 nm, about 390 nm to about 400 nm, about 400 nm to about 410 nm, about 410 nm to about 420 nm, about 420 nm to about 430 nm, about 430 nm to about 440 nm, about 440 nm to about 450 nm, about 450 nm to about 460 nm, about 460 nm to about 470 nm, about 470 nm to about 480 nm, about 480 nm to about 490 nm, or about 490 nm to about 500 nm, as well as any combination thereof, such as, for example, 130 nm to 250 nm.

The magnetically-susceptible core particles may be constructed of any material capable of functioning in accordance with the presently disclosed and claimed inventive concept(s). Non-limiting examples of materials from which the particles may be constructed include $Fe_3O_4$ (magnetite), gamma-$Fe_2O_3$ (maghemite), alpha-$Fe_2O_3$ (hematite), FeNi, FePt, and/or Fe—CoNi alloy. In one embodiment the magnetically-susceptible core particles of the MNPs are superparamagnetic; that is, they are non-magnetic unless exposed to (placed within) an external magnetic field. Typically, the magnetically-susceptible core particles have diameters in the range of about 10 nm to about 15 nm.

In one embodiment of the presently disclosed and claimed inventive concept(s), MNPs carrying the calcium compound are magnetically targeted to one, two, three, or four of the major atrial GP in the heart. This approach is designed to cause apoptosis and death of the one or more GPs so as to cease the vicious cycle of atrial remodeling, which allows AF to perpetuate itself. Further, using this approach, collateral damage to the surrounding atrial myocardium and intrinsic CANS is minimized. The magnetic targeting approach described herein is safer and substantially less expensive than catheter or surgical ablation, preventing the progression from paroxysmal to persistent AF, which carries much higher risks of morbidities such as stroke. In one embodiment, a focused external magnetic field and gradient is used to concentrate intravascularly-injected MNPs in one or more of the major atrial GP to treat patients with AF. Where the MNPs are described herein as being targeted to a GP, it is intended to refer to targeting MNPs to a portion or region of the heart which contains the GP, as well as referring to specifically targeting the GP itself. Further where the treatment is described as applying a magnetic field and gradient to the GP, it is intended to refer to applying a magnetic field and gradient to a portion or region of the heart which contains the GP, as well as referring to applying the magnetic field and gradient specifically to the GP itself.

As described herein, in one non-limiting embodiment of the presently disclosed and claimed inventive concept(s), the goal is targeted calcium delivery to the GP in order to treat AF. MNPs are synthesized or provided that contain: (1) a matrix component (which may optionally be thermolabile), (2) one or more magnetically-susceptible core particles (superparamagnetic particles) disposed within the matrix component, and (3) a calcium payload, also disposed within the matrix component. In the presence of an external magnetic field, this construct enables magnetic capture of the MNPs at the targeted GP site and allows calcium ions to be released into the epicardial site to ablate the neural elements in the GP.

One embodiment of the presently disclosed and claimed inventive concept(s) comprises a method that uses MNPs comprising: (a) poly(lactic-co-glycolic acid) (PLGA) or other polymeric material described herein as a matrix component, (b) magnetically-susceptible core particles, such as magnetite, which are disposed within the matrix component, and (c) an ionizable calcium compound which is releasably incorporated into the matrix component.

In certain embodiments, the presently disclosed and claimed inventive concept(s) include methods for the in vivo delivery of a calcium compound to the heart. In the method, a pharmaceutical composition is provided that contains superparamagnetic, targetable MNPs (as described elsewhere herein) disposed in a pharmaceutically-acceptable carrier or vehicle (such as but not limited to, a vehicle suitable for injection). The pharmaceutical composition is administered to a patient by any method known in the art that allows the pharmaceutical composition to function in accordance with the presently disclosed and claimed inventive concept(s); in one non-limiting embodiment, the pharmaceutical composition is injected into the patient. After administration of the pharmaceutical composition, a magnetic field and gradient of appropriate strength and magnitude sufficient to guide and retain a portion of the MNPs at a site of interest, such as but not limited to one or more GPs of the heart, is established.

As used herein, the term "pharmaceutically acceptable" refers to those properties and/or substances which are acceptable to the patient from a pharmacological/toxicological point of view, including bioavailability and patient acceptance, or are acceptable to the manufacturing chemist from a physical-chemical point of view regarding composition, formulation, stability, and isolatability thereof. Phosphate-buffered saline (PBS) is one non-limiting example of a pharmaceutically acceptable carrier or vehicle. Suitable injectable solutions include, but are not limited to, intravenous, subcutaneous, and intramuscular injectable solutions. Non-limiting examples of injectable forms include solutions, suspensions, and emulsions. Other pharmaceutically acceptable carriers include but are not limited to Ringers solution, dextrose solution, or other aqueous carrier known in the art. Appropriate non-aqueous carriers may also be used, and non-limiting examples thereof include cyclodextrins (such as but not limited to hydroxypropyl beta cyclodextrin), mixed oils (such as but not limited to, vitamin E oil), polyethylene glycol, and ethyl oleate. One particular non-limiting carrier that may be utilized in accordance with the presently disclosed and claimed inventive concept(s) includes cyclodextrin in water. In some embodiments additives are included in the carrier, such as but not limited to, buffers, preservatives, and other substances that enhance isotonicity and chemical stability.

The calcium compound, magnetic core, and polymer shell may be present in the MNPs at any concentration that allows the MNPs to function in accordance with the presently disclosed and claimed inventive concept(s). In non-limiting exemplary MNPs, the calcium compound may be present in a range of from about 1% to about 75% by weight, the magnetic core particles may be present in a range of from about 5% to about 50% by weight, and the matrix component may be present in a range of from about 5% to about 75% by weight.

The term "matrix component" as used herein is meant to include any synthetic and/or natural polymeric material which is biocompatible and that can be used in vivo as the matrix which surrounds and/or contains the magnetically-susceptible core particles and calcium compound of the MNPs used herein. The matrix component may be bioinert and/or biodegradable. Some non-limiting examples of polymeric materials that may be utilized in accordance with the presently disclosed and claimed inventive concept(s) include polylactides, polyglycolides, polycaprolactones, polydioxanones, polycarbonates, polyhydroxybutyrates, polyalkylene oxalates, polyanhydrides, polyamides, polyacrylic acid, polyoxamers, polyesteramides, polyurethanes, polyacetals, polyorthocarbonates, polyphosphazenes, polyhydroxyvalerates, polyalkylene succinates, poly(malic acid), poly(amino acids), alginate, agarose, chitin, chitosan, gelatin, collagen, dextran, proteins, and polyorthoesters, and copolymers, terpolymers, and combinations and mixtures thereof.

The matrix component may be in the form of a hydrogel, which is defined herein as a water-containing polymeric network. The polymers used to prepare hydrogels can be based on a variety of monomer types, such as, but not limited to, those based on methacrylic and acrylic ester monomers, acrylamide (methacrylamide) monomers, and N-vinyl-2-pyrrolidone. Hydrogels can also be based on polymers such as, but not limited to, starch, ethylene glycol, hyaluronan, heparosan, chitose, and/or cellulose. To form a hydrogel, monomers are typically crosslinked with crosslinking agents such as, but not limited to, ethylene dimethacrylate, N,N-methylenediacrylamide, methylene bis(4-phenyl isocyanate), epichlarohydin glutaraldehyde, ethylene dimethacrylate, divinylbenzene, and allyl methacrylate. In addition, hydrogels can be formed from mixtures of monomers and polymers.

Another type of polymeric network used herein as the matrix material can be formed from one or more hydrophobic monomers and/or macromers. Matrices formed from these materials generally exclude water. Polymers used to prepare hydrophobic matrices can be based on a variety of monomer types such as, but not limited to, alkyl acrylates and methacrylates, and polyester-forming monomers such as ε-caprolactone, glycolide, lactic acid, glycolic acid, and lactide. When formulated for use in an aqueous environment, these materials do not need to be crosslinked, but they can be crosslinked with standard agents such as, but not limited to, divinyl benzene. Hydrophobic matrices can also be formed from reactions of macromers bearing the appropriate reactive groups, such as but not limited to, the reaction of diisocyanate macromers with dihydroxy macromers, and the reaction of diepoxy-containing macromers with dianhydride or diamine-containing macromers.

The matrix component, as noted elsewhere herein, may be biodegradable, bioresorbable, bioinert, and/or biostable. Bioresorbable hydrogel-forming polymers are generally naturally occurring polymers such as polysaccharides, examples of which include but are not limited to, hyaluronic acid, starch, dextran, alginate, heparin, and chitosan; and proteins (and other polyamino acids), examples of which include but are not limited to, gelatin, collagen, fibronectin, laminin, albumin, and active peptide domains thereof and combinations thereof. Matrix components formed from these materials degrade under physiological conditions, generally via enzyme-mediated hydrolysis.

Bioresorbable matrix components which can be used herein are generally synthetic polymers prepared via condensation polymerization of one or more monomers. Matrix-forming polymers of this type include, but are not limited to, polylactide (PLA), polyglycolide (PGA), poly(lactide-co-glycolide) (PLGA), and polycaprolactone (PCL), as well as copolymers of these materials, polyanhydrides, and poly-ortho esters, and combinations thereof.

Biostable or bioinert hydrogel matrix-forming polymers which can be used herein as the matrix component are generally synthetic or naturally occurring polymers which are soluble in water, matrices of which are hydrogels or water-containing gels. Non-limiting examples of this type of polymer include, but are not limited to, polyvinylpyrrolidone (PVP), polyethylene glycol (PEG), polyethylene oxide (PEO), polyacrylamide (PAA), polyvinyl alcohol (PVA), and combinations thereof.

Biostable or bioinert matrix-forming polymers which can be used herein as the matrix component are generally synthetic polymers formed from hydrophobic monomers, such as but not limited to, methyl methacrylate, butyl methacrylate, dimethyl siloxanes, and the like. These polymer materials generally do not possess significant water solubility but can be formulated as neat liquids which form strong matrices upon activation. It is also possible to synthesize polymers which contain both hydrophilic and hydrophobic monomers.

The matrix component can optionally provide a number of desirable functions or attributes. For example but not by way of limitation, the polymers can be provided with water soluble regions, biodegradable regions, hydrophobic regions, as well as polymerizable regions.

In particular non-limiting embodiments, the matrix component of the presently disclosed and claimed inventive concept(s) may include any of the following: poly (glycolic acid), poly (DL-lactic acid), poly (lactic acid-co-glycolic acid) copolymer (PLGA), poly (ε-caprolactone), the poly (alkylcyanoacrylate) family, poly (isobutylcyanoacrylate), poly (ethylcyanoacrylate), polyethylenimine, poly (β-aminoesters), quaternary ammonium polysaccharides, poly (N-isopropylacrylamide i.e., PNIPA-Am), poly (N-isopropylmethacrylamide-co-acrylamide) copolymer, polyhydroxybutyrate, poly (ester-amide), poly (methylidene malonate), polyglutaraldehyde, poly (N-isopropylacrylamide)/poly (ethyleneimine) copolymer, PNIPA-Am/poly[N-(2-hydroxypropyl) methacrylamide] copolymer, PNIPA-Am-co-acrylamide-block-polyallylamine copolymer, PNIPA-Am-co-methylmethacrylate-co-methacrylic acid, poly[2-dimethyl(aminoethyl)methacrylate] (PDMAEM), PNIPA-Am/PDMAEM copolymer, PNIPA-Am-co-DMSO copolymer, PNIPA-Am-co-N,N-dimethylaminopropyl acrylamide-co-butylmethacrylate copolymer, poly (methacrylic acid-co-hydroxyethyl methacrylate copolymer, polyvinylbenzyl-o-β-galactopyranosyl-D-glucosamide copolymer, Polyethylene glycol (PEG), PEG-silane copolymer, fluidMAG-particles (chemicell GmbH, Berlin, Germany), poly (N,N-dimethylacrylamide), PLURONIC® F127 (BASF Corp., North Mount Olive, N.J.), carboxymethyl dextran, PEGylated amphiphilic triblock copolymer, gum Arabic, gum tragacanth, 2-(acetoacetoxy) ethyl methacrylate, poly (ethylene) glycol methylether methacrylate, chitosan triphosphate, chitosan triphosphate-hyaluronic acid, polyvinyl acetate, poly (vinylpyrrolidone), $SiO_2$-polymethylmethacrylate, poly [oligo(ethyleneglycol)methacrylate-co-methacrylic acid], poly (N-vinylacetamide) (NVA), PNIPAAmco-NVA copolymer, Dextron-poly (ε-caprolactone)-2-hydroxyethyl methacylate-PNIPAAm copolymer, PNIPAAm-PEG copolymer, poly (ethyl-2-cyanoacrylate), poly (butylcyanoacrylate), poly (hexylcyanoacrylate), poly (octylcyanoacrylate), heparin compounds, hyaluronic acid, and poly (3-(trimethoxysilyl)propyl methacrylate-r-PEG methyl ether methacrylate-r-N-acryloxysuccinimide), and any combination of the above.

One or more appropriate calcium compounds are incorporated within the matrix component of the MNPs for delivery to specific sites, for example, under control of a magnetic field. The calcium compound can be embedded, contained within, or adsorbed or absorbed on or within the matrix component (such as but not limited to, a hydrogel or a block copolymer), and permitted to diffuse therefrom at a controlled rate. The rate of diffusion of the calcium compound can be controlled by varying the composition of the matrix component and/or by varying the magnetic field or gradient as discussed elsewhere herein.

The term calcium compound is intended to cover any calcium compound which is ionizable to form $Ca^{2+}$ ions and includes, but is not limited to, at least one of calcium chloride ($CaCl_2$), calcium carbonate ($CaCO_3$), calcium citrate, calcium gluconate, calcium formate, calcium citrate malate, calcium bis-glycinate, calcium lactate, calcium orotate, calcium fumarate, calcium fluoride, calcium ascorbate, calcium succinate, and calcium aspartate, as well as any combination thereof.

The MNPs produced and utilized as described herein may assume any shape that allows them to function in accordance with the presently disclosed and claimed inventive concept(s). In certain non-limiting embodiments, the MNPs may be in the shape of a cylinder, a cylindrical rod, a worm, a circular disc, a sphere, an ovoid, an irregular shape, or a combination thereof.

In certain embodiments of the method of the presently disclosed and claimed inventive concept(s), once the MNPs have been magnetically drawn to the desired area of the ANS, such as but not limited to, the stellate ganglia, the ligament of Marshall, or one or more of the atrial GP of the cardiac ANS, the magnetic force applied to the MNPs can be changed from static to oscillating (e.g., alternating). This change causes the MNPs to become warmer, above normal physiologic temperatures (i.e., above 37° C.), thereby causing an increase in the release of the calcium compound from the matrix component of the MNPs in a phenomenon referred to herein as "magnetothermally-triggered release." This may be induced, for example but not by way of limitation, at about 100 Hz to about 300 Hz.

In regard to the types of magnets which can be used herein, the pole face field strength may be, in one particular non-limiting embodiment, about 2600 milli-Tesla (mT) to about 4600 mT. The magnetic gradient in one non-limiting embodiment is in a range of from about 2 T/meter to about 10 T/meter. When the magnet is an electromagnet, the duty cycle of the electromagnet can range, for example but not by way of limitation, from about 10% to about 33%. Its output can be a square wave or a balanced wave form, equal upward and downward, representing a change in polarity. In regard to the strength of the magnetic field strength to be applied at the MNP capture point in the coronary micro-circulation, one embodiment of a particular range is about 100 mT to about 400 mT. Ranges of frequencies of oscillations to be applied include, by way of example but not by way of limitation, from about 100 to about 200 Hz or from about 200 to about 400 Hz for heating of local tissue in the vicinity of the MNPs that were targeted to that site.

In an alternative version of the presently disclosed and claimed inventive concept(s), once the MNPs with the calcium compound are located in the targeted area of the ANS (such as but not limited to, neuronal tissue of the heart), neurons may be killed by magnetically heating the MNPs to a temperature at which the neuronal tissue dies. Non-limiting exemplary heated temperatures are in a range from about 49° C. to about 55° C. (where normal physiologic temperature is ≤38° C.). This can be induced by exposure of the MNPs to a frequency of from about 200 to about 400 Hz, for example.

In a another aspect of the presently disclosed and claimed inventive concept(s), the MNPs can gather as clumps within blood vessels (microvessels) of the GPs, causing ischemia of the tissues supplied by said blood vessels, wherein multiple emboli act with the calcium ions to kill neurons in the affected tissues. The propensity for causing the MNPs to aggregate and clump and block the microvessels' flow (microembolization) can be increased by increasing the magnetic field strength and/or the magnetic field gradient at that preferred embolic site. The size of the aggregates may be for example but not by way of limitation, in a range of from about 100 nm to about 900 nm in diameter (such as but not limited to, from about 100 nm to about 300 nm in diameter or from about 300 nm to about 900 nm in diameter, or any variation there between). The sizes of agglomerations of the aggregates in microvessels may be the size of the inside diameter of the vessels, such as but not limited to, about 1 micrometer to about 10 micrometers in width and about 1 cm to about 2 cm in length.

In general, during a single treatment comprising the method of the presently disclosed and claimed inventive concept(s), the magnetic field and gradient is applied to the specific portions of the ANS for non-limiting, exemplary duration periods of from about 10 minutes to about 6 hours, from about 20 minutes to about 4 hours, and from about 30 minutes to about 2 hours, although it will be understood that the magnetic field or gradient can be applied, for other duration periods, and non-limiting duration periods encompassed by the scope of the presently disclosed and claimed inventive concept(s) include about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 minutes, or any integeric minute there within, such as 37 or 152 minutes, or any range of such minutes, such as for example 10 to 60 minutes.

In another embodiment, the magnetic field or gradient is applied to the MNPs for targeting the MNPs in association with concurrent application of Magnetic Resonance Imaging (MRI), for example, in a manner shown in U.S. Published Patent Application 2010/0079142, the entirety of which is incorporated by reference herein.

In one embodiment, the MNPs are administered in a treatment protocol comprising multiple doses, administered simultaneously, consecutively, or sequentially over time. One non-limiting example of a treatment protocol includes a first treatment comprising one or two doses, optionally followed by another treatment in about 6-12 months (e.g., about 6-8 months or about 8-10 months), and optionally followed by one to three similar treatments administered after similar durations of time. In one non-limiting embodiment, the concentration of the calcium compound of the MNPs is in a range of about 10 ng to about 10 mg per dose, or is in a range of about 100 ng to about 1 mg per dose. In one version of the presently disclosed and claimed inventive concept(s), the magnetic field and gradient applied to the MNPs causes the MNPs to move through the myocardial tissues at a velocity in a range of, but not limited to, about 0.01 to about 0.1 mm/min. In specific embodiments the velocity may be at least about 0.01 mm/min, at least about 0.02 mm/min, at least about 0.03 mm/min, at least about 0.04 mm/min, at least about 0.05 mm/min, at least about 0.06 mm/min, at least about 0.07 mm/min, at least about 0.08 mm/min, at least about 0.09 mm/min, or at least about 0.10 mm/min, for example.

Additionally, the contractions of the myocardium while the heart is beating also facilitate movement of the drug, and the MNPs, through the myocardium, in the direction of the stronger magnetic field and gradient and down the field and gradient.

Generally, the magnetic field and gradient may be applied externally to the body, on or near the surface of the chest or other area of the ANS to be targeted.

In one embodiment, the magnet or electromagnet pulls the MNP into the region of the ANS (e.g., the cardiac ANS) where body temperature causes the matrix component (e.g., poly NIPPA, or other thermolabile material) to release the calcium compound. This heat lability is a property of the particle's matrix component.

As noted above, once the MNPs are pulled into position near the targeted region, e.g., the ganglionated plexi, the electromagnet can be adjusted to present an alternating magnetic field of known frequencies to cause warming of the MNPs by oscillating the magnetite (or other ferrous material in the core), then using the magnet to accelerate the release of the calcium compound for a controlled release of the therapeutic. Furthermore, the tissue in the vicinity of the ganglionated plexi is warmed by the oscillation of the nanoparticles.

The quantitative denervation, which corrects the autonomic imbalance of neural control of the targeted ANS, may be accomplished both by release of the calcium compound in the targeted tissue (e.g., the ganglionated plexi such as the ARGP), and additionally (and potentially synergistically) by the embolization of the microvessels serving the targeted site of the ANS. This embolization is caused by magnetic capture and holding of the superparamagnetic nanoparticles carrying the compound MNPs in the vicinity of the GP so that blood flow thereto is reduced, thereby causing ischemia and subsequent death of neurons in the targeted area.

As noted elsewhere herein, the intrinsic body temperature or magnetic oscillation of the magnetic field or gradient can induce heating of thermolabile forms of the matrix component of the MNPs to the lower critical solution temperature (LCST) of the polymer, thereby inducing release of the calcium compound into the circulation. The level of heating necessary to reach the LCST can be established by the chemical formulation and determined by a person of ordinary skill in the art. In one embodiment, the LCST of the matrix component is set by its formulation at body temperature, so that when the particles are warmed to about 38° C., they will begin to release the calcium compound. This keeps the solution stable at room temperature, and the calcium compound will not be released prematurely on the shelf. If warmed to the LCST by magnetic oscillations, the release will be accelerated and under the control of the magnet. If the particles are warmed above the LCST, this will assure that all or most of the calcium payload is released. It is known that neurons are labile to excessive heat. As noted elsewhere herein, if the tissue in the region of the GP is heated to about 48-50° C., then neurons therein will begin to die (before cardiac cells).

The external source of a magnetic field and gradient of the presently disclosed and claimed inventive concept(s) is capable of (i) magnetizing the superparamagnetic particle and (ii) increasing a degree of magnetization of the MNPs and thereby increasing the force of attraction. Those skilled in the art using guidance provided in this disclosure will be able to select the proper magnetic source and its capabilities without undue experimentation. One particular external source is an electromagnet.

In one embodiment related to targeting a portion of the ANS of the heart (the intrinsic CANS), catheterization of the heart into the arteries supplying the stellate ganglia, the ligament of Marshall or GP can be made in the subject and is done readily every day by interventionalists performing angiography of the coronary vessels. Such a catheter can be used to release a dosage of a solution of the MNPs that will flow downstream towards the target cardiac tissue containing a ganglionated plexi desired to be targeted, such as the anterior right GP (ARGP). At the ARGP, or other GP, a magnetic field and gradient will be present, caused either by a permanent magnet or electromagnet, which is generally located outside of the chest but in certain embodiments may be placed internally in the chest of a patient.

Specific non-limiting examples of MNPs comprise a composite containing magnetite, a biocompatible, magnetically susceptible iron oxide that is superparamagnetic. The diameters of the magnetically-susceptible core particles in this example are in a range of about 10-15 nm. Single or multiple magnetite particles may be encapsulated in the matrix component to form a single MNP. Thus, when the calcium compound containing magnetite particles are in the region of the GP, they respond to the magnetic field and gradient and are captured in the GP microcirculation subserving the GP; the MNPs are then held there as long as there is a magnetic field and gradient present. Once magnetically captured the MNPs are pulled from the coronary microcirculation into the epicardium containing the GP (i.e., completion of targeting), toward the pole face of the magnet. Next, the calcium compound begins to be released and begins to decrease the autonomic neural activity in the GP by causing apoptosis of neural cells.

In one embodiment of the presently disclosed and claimed inventive concept(s), MNPs are synthesized that are made of magnetically-susceptible core particles that include $Fe_3O_4$, a matrix component comprising a thermo-responsive polymeric hydrogel, and the calcium compound. To synthesize the MNPs, the magnetically-susceptible core particles (e.g., magnetite) are formed by co-precipitation of ferrous and ferric salts in the presence of basic solution and docusate sodium salt as a surfactant. Then, the magnetic nanoparticles are coated with vinyltrimethoxysilane via acid catalyst hydrolysis followed by electrophilic substitution on the surface of the MNP forming a magnetic core. Poly-N-isopropylacrylamide-co-acrylamide (pNIPA-AAm), a thermo-responsive hydrogel, is then polymerized on the magnetic core via a silane coupling agent and radical polymerization method. This process allows a strong attachment of the magnetic core with the polymeric hydrogel matrix component, thereby preventing the magnetically-susceptible core particles of the magnetic core of the MNP from diffusing out of the matrix component and also permitting the encapsulation of a calcium compound. The lower critical solution temperature (LCST), the temperature above which the hydrogel contracts and disintegrates, is formulated at 37° C., allowing for enhanced calcium release only at body temperature.

In another non-limiting embodiment, MNPs comprising PLGA, magnetite, and a calcium compound are prepared by a single emulsion (oil-in-water) technique. In one embodiment the MNPs can be produced by the following process: (1) add 100 mg of PLGA to 5 ml of dichloromethane (DCM) to form the oil/organic phase, (2) add 10 mg of iron oxide nanoparticles and sonicate the resultant solution at 20 W for 8 minutes, add 10-500 mg of a calcium compound, (e.g., $CaCl_2$ or any other calcium compound contemplated herein) during step 1 or 2, (3) add the PLGA-iron oxide solution dropwise to the aqueous phase consisting of 1 g PVA in 20 ml DI water, (4) sonicate this suspension for 5 minutes at 50 W (using ice batch to prevent the heat from sonication) to form nanoparticles, (5) take the particle suspension out and keep for stirring overnight to allow evaporation of DCM, (6) use a magnet to collect the iron-containing particles and remove excess surfactant and polymers (washing step: repeat twice with DI water), (7) centrifuge the solution at 1000 rpm for 1 minute to remove unbound iron oxide aggregates (the pellet after centrifugation containing mostly unbound iron oxide aggregates), (8) collect the supernatant after centrifugation (nanoparticle suspension) and proceed to lyophilization to collect the PLGA-MNPs.

Nanoparticles with superparamagnetic properties have attracted clinical attention for drug delivery because of their unique property that they magnetize strongly in the presence of an external magnetic field but retain no permanent magnetism after the magnetic field is removed. Thermoresponsive hydrogels based on pNIPA-AAm have been synthesized and functionalized previously. It is contemplated herein that at temperatures above the lower critical solution temperature (LCST), a pNIPA-AAm hydrogel will shrink by expelling water molecules, thereby releasing the calcium compounds incorporated in the hydrogel. In one embodiment the MNPs comprising pNIPA-AAm have a LCST at 37° C.

In one non-limiting example, the composition of MNPs comprises 1 mg/ml of MNPs in solution, which comprise about 30% magnetite (by mass), about 50% of a calcium compound such as $CaCl_2$ (by mass), and about 20% of PLGA (by mass). In this embodiment, the magnetite comprises about 300 micrograms/ml, the $CaCl_2$ comprises about 500 micrograms/ml, and the PLGA comprises about 200 micrograms/ml. The amount of injected MNPs is 1 mg provided in 1 ml of injectate. About 40% of the $CaCl_2$ is released from the PLGA polymer shell within about 2-3 hours, and the remainder is released over a period of days thereafter.

Although the presently described inventive concept(s) have been described in detail, it should be understood that various changes, substitutions, and alterations can be made herein without departing from the spirit and scope of the presently described inventive concept(s) as defined in the appended claims. Moreover, the scope of the presently described inventive concept(s) is not intended to be limited to the particular examples and embodiments of the process, items of manufacture, compositions of matter, means, methods and steps described in the specification. As one of ordinary skill in the art will readily appreciate from the present disclosure, processes, items of manufacture, compositions of matter, means, methods, or steps, presently existing or later to be developed that perform substantially the same function or achieve substantially the same result as the corresponding examples and embodiments described herein may be utilized according to the presently described inventive concept(s). Accordingly, the appended claims are intended to include within their scope such processes, items of manufacture, compositions of matter, means, methods, or steps.

What is claimed is:

1. A method of treating a cardiovascular disorder in a subject in need of such treatment, the method comprising the steps of:
    administering magnetic nanoparticles to a vascular component of the subject, wherein each magnetic nanoparticle comprises:
        (1) one or more magnetically-susceptible core particles comprising magnetite,
        (2) a biocompatible matrix component which contains the magnetically-susceptible core particles and comprises a polymer shell,
        (3) a calcium payload adsorbed onto the polymer shell of the biocompatible matrix, the calcium payload comprising a calcium compound able to release calcium ions in vivo, wherein the calcium compound comprises calcium chloride ($CaCl_2$), and
        wherein the calcium compound of the calcium payload and the magnetically-susceptible core particles are separate components; and
    applying a magnetic gradient to a body of the subject at a position in a vicinity of a targeted portion of the autonomic nervous system (ANS) of the subject, the magnetic gradient causing the magnetic nanoparticles to move into and be magnetically captured in the targeted portion of the ANS; and
    wherein calcium ions released from the calcium payload induce a neuropathy in the targeted portion of the ANS and thereby treat the cardiovascular disorder in the subject.

2. The method of claim 1, wherein the magnetically-susceptible core particles of the magnetic nanoparticles comprise a superparamagnetic material.

3. The method of claim 1, wherein the vascular component is an artery.

4. The method of claim 1, wherein the vascular component is a vein.

5. The method of claim 1, wherein the magnetic nanoparticles have a major diameter in a range of from about 150 nm to about 500 nm.

6. The method of claim 5, wherein the magnetically-susceptible core particles have a major diameter in a range of from about 10 nm to about 15 nm.

7. The method of claim 1, wherein the biocompatible matrix component is biodegradable.

8. The method of claim 1, wherein the targeted portion of the ANS comprises at least one ganglionated plexi.

9. The method of claim 8, wherein the at least one ganglionated plexi is selected from the anterior right ganglionated plexi, the inferior right ganglionated plexi, the superior left ganglionated plexi, the inferior left ganglionated plexi, the ligament of Marshall, the left stellate ganglion, and the right stellate ganglion.

10. The method of claim 1, wherein the targeted portion of the ANS is at least one portion of the ventrolateral cardiac nerves, the vein of Marshall, and the renal arterial sympathetic nerves and neurons that control blood pressure.

11. The method of claim 1, wherein the targeted portion of the ANS is the PV-atrial junction.

12. The method of claim 1, wherein the cardiovascular disorder is at least one of an atrial disorder, a ventricular disorder, vasovagal syncope, a sinus nodal disorder, and hypertension.

13. The method of claim 1, wherein the magnetic nanoparticles are administered as a composition comprising the magnetic nanoparticles disposed in a pharmaceutically-acceptable carrier or vehicle.

* * * * *